United States Patent [19]

Uedo et al.

[11] Patent Number: 5,093,372
[45] Date of Patent: Mar. 3, 1992

[54] NOVEL PHARMACEUTICAL COMPOSITION COMPRISING EXIFONE AND WATER-SOLUBLE POLYMER

[75] Inventors: Yoshio Uedo, Kobe; Fumio Shimojo, Kawanishi; Mitsuru Yasumara, Nishinomiya; Kenzo Toyoshima, Ikoma; Nobumitsu Nakahasi, Kadoma, all of Japan

[73] Assignee: Fujisawa Pharmaceutical Co. Inc., Osaka, Japan

[21] Appl. No.: 488,492

[22] Filed: Mar. 2, 1990

Related U.S. Application Data

[63] Continuation of Ser. No. 259,287, Oct. 18, 1988, abandoned.

[30] Foreign Application Priority Data

Nov. 11, 1987 [JP] Japan ................. 62-284493

[51] Int. Cl.$^5$ ............................ A61K 31/12
[52] U.S. Cl. ................... 514/687; 514/685; 514/686; 514/781; 424/488; 424/489
[58] Field of Search ............ 424/78, 488, 489; 514/781, 687, 685, 686

[56] References Cited

U.S. PATENT DOCUMENTS

| | | | |
|---|---|---|---|
| 4,015,017 | 3/1977 | Gazave et al. | 514/685 |
| 4,145,440 | 3/1979 | Fitch et al. | 514/781 |
| 4,412,986 | 11/1983 | Kawata et al. | 514/781 |

FOREIGN PATENT DOCUMENTS 49-118825  11/1974  Japan .................. 514/781

OTHER PUBLICATIONS

CA 89(22): 186079y, "Drugs contg. 2,3,4,3',4", 5" Hexahydroxybenzophenone" 1978, Laboratories Pharmascience.

CA 107(13):109260p, "The Effects of Cxifone, New Agent for Senile Memory Disorder," Porsolt et al., 1987.

Sugimoto et al., "Dissolution & Absorption of Nifedipine from Nifedipine-PVP Copreaprtate", Drug Development & Ind. Pharmacy 6(2) 137-160 (1980).

Mizobe et al., "Application of Solid Dispersion to Enhance Dissolution Rate & Bioavailability of Bisbentiamine in Enteric Tablets", vol. 43, #1 (1983).

*Primary Examiner*—F. T. Moezie
*Attorney, Agent, or Firm*—Jordan B. Bierman

[57] ABSTRACT

A pharmaceutical composition which is a physical mixture of exifone and certain water soluble cellulose derivatives. The mixture exhibits surprisingly improved solubility and bio availability.

2 Claims, No Drawings

NOVEL PHARMACEUTICAL COMPOSITION COMPRISING EXIFONE AND WATER-SOLUBLE POLYMER

This application is a continuation of application Ser. No. 259,287, filed Oct. 18, 1988 now abandoned.

The present invention relates to a novel pharmaceutical composition comprising exifone and a water-soluble polymer, which improves low absorbability of exifone upon oral administration, and so is useful in the pharmaceutical field.

Exifone, which has the structure shown below, is useful as a cerebral metabolic improving agent and effective, for example, in the treatment of senile dementia, cerebrovascular dementia and the like.

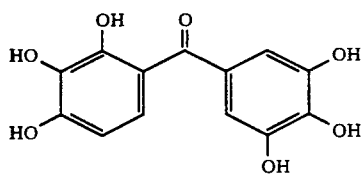

However, exifone is sparingly soluble in water (saturated solubility: about 70–80 μg/ml) and has disadvantage that when it is orally administered as a conventional pharmaceutical composition, its absorption into blood circulation is poor and accordingly its bioavailability is low. Therefore, the advent of a novel pharmaceutical composition which can overcome this drawback has been awaited.

The inventors of the present invention found that the above drawback can be overcome by compounding exifone and a water-soluble polymer, and as a result of our intensive investigations, we have completed the present invention.

The present invention is the first that has overcome the above drawback of exifone.

The novel pharmaceutical composition of the present invention is characterized in that it comprises exifone and a water-soluble polymer. By the coexistence of exifone and a water-soluble polymer the drawback that exifone is sparingly soluble in water is improved and high bioavailability can be attained upon oral administration.

The pharmaceutical composition of the present invention may further contain, if necessary, conventional additive(s) used ordinarily in the process of making up pharmaceutical compositions, such as disintegrants, lubricants, excipients, colorants, and so forth. The dosage form is not critical, thus, upon oral administration, the composition can be used, as desired, in the form of powders, fine granules, granules, capsules, tablets, film-coated tablets and so forth.

Suitable examples of the water-soluble polymer to be used in this pharmaceutical composition may include those ordinarily used in this field of the art, such as, for example, cellulose derivatives (e.g. hydroxypropylmethylcellulose, hydroxypropylcellulose, methylcellulose, etc.), synthetic water-soluble polymer (e.g. polyvinylpyrrolidone, etc.) and the like. Among these, the more preferred one may be cellulose derivatives and the most preferred one may be hydroxypropylmethylcellulose and hydroxypropylcellulose.

Suitable disintegrants may include, for example, starch species (e.g. potato starch, corn starch, hydroxypropylstarch, carboxymethylstarch sodium, etc.), cellulose derivatives (e.g. carboxymethylcellulose calcium, carboxymethylcellulose, low substituted hydroxypropylcellulose, etc.) and the like. Suitable lubricants may include, for example, talc, wax species (e.g. white beeswax, hardened oils, etc.), stearic acid species (e.g. stearic acid, magnesium stearate, calcium stearate, etc.) and the like. Suitable excipients may include, for example, sugars (e.g. lactose, sucrose, etc., starch species e.g. corn starch, etc.), cellulose derivatives (e.g. microcrystalline cellulose, etc.), inorganic calcium salts (e.g. calcium hydrogen phosphate, calcium sulfate, etc.) and the like and suitable colorants may include, for example, tar dyes and the like. The additives are not limited to the examples mentioned above, but any additives conventionally used in this field of the art may be used.

The pharmaceutical composition of the present invention which comprises exifone and a water-soluble polymer can be produced by compounding exifone and the above-mentioned water-soluble polymer, if necessary, together with the above-mentioned conventional additive(s), and then converting the mixture to a desired dosage form.

The process for the preparation of the pharmaceutical composition of the present invention by compounding exifone and water-soluble polymer, etc. may include the process to convert these substances to a solid dispersion composition and the process to mix these substances, and both processes are described in detail hereinbelow.

PROCESS TO CONVERT THE SUBSTANCES TO A SOLID DISPERSION COMPOSITION

The pharmaceutical composition of the present invention can be produced by converting exifone to a solid dispersion composition.

In order to convert exifone and a water-soluble polymer, if necessary, together with a conventional additive(s) to a solid dispersion composition, any procedure conventionally used in this field of the art may be used.

Thus, for instance, said composition can be produced by dissolving exifone in an appropriate organic solvent (e.g. ethanol), then adding to and dissolving or uniformly dispersing in this solution the water-soluble polymer, and after that evaporating the solvent and drying by a conventional method. When the water-soluble polymer is not satisfactorily dissolved in a solvent upon its addition thereto, another organic solvent (e.g. methylene chloride) may be added so as to dissolve it. The solvent may be selected depending upon the kind of the water-soluble polymer employed.

When above-mentioned conventional additive(s) are compounded, they may be incorporated into the composition simultaneously as the water-soluble polymer is dispersed in the composition. Alternatively, after preparation of a solid dispersion composition composed of exifone and a water-soluble polymer, said additive(s) may be compounded with said solid dispersion composition.

The thus-obtained solid dispersion composition comprising exifone and a water-soluble polymer can be converted to various dosage forms by steps conventionally used in this field of the art, for example, milling sieving, kneading, granulating, tableting, coating, etc. These steps may be carried out in the conventional manner.

PROCESS TO MIX THE SUBSTANCES

The pharmaceutical composition of the present invention can be produced by mixing exifone with a water-soluble polymer, if necessary, together with a conventional additive(s).

The means of mixing to be used in this process may be any means conventionally employed in this field of the art. For further decreasing the particle size, the resulting mixture may be milled. The milling can be performed by a conventional method.

The thus-produced mixture comprising exifone and a water-soluble polymer, etc., if desired, can be converted to various dosage forms by the steps mentioned above for the Process to convert the substances to a solid, dispersion composition.

This process, Process to mix the substances, is suitable for industrial production because of its being easy to perform.

In producing the pharmaceutical composition of the present invention by this process, it is particularly preferable to knead the mixed powder with a suitable kneading solvent and then convert the kneaded matter to the desired dosage form. Suitable kneading solvents may include water, ethanol, and mixtures thereof.

The pharmaceutical composition of the present invention which comprises exifone and a water-soluble polymer can be produced by the above-mentioned processes. In its production, the kind and the amount of the water-soluble polymer and additive(s) to be used can be selected suitable depending, for example, upon the desired dosage form, the content of exifone therein, the desired dissolution pattern of exifone, and so forth.

When the water-soluble polymer to be used is a cellulose derivative, for instance, the compounding ratio of exifone and the water-soluble polymer is preferably about 1:0.01 to about 1:7 by weight, more preferably 1:0.05 to 1:5 by weight.

When a water-soluble polymer of another kind is used, it is possible for those skilled in the art to determine an appropriate compounding ratio with ease by studying the dissolution pattern, etc. of the composition.

In the following, the present invention is explained in detail by Examples. [I] Process to convert the substances to a solid dispersion composition.

EXAMPLE 1

Exifone (10 g) was dissolved in ethanol (150 ml). To this solution was added TC-5R (5 g) (trademark, product of Shin-Etsu Chemical; generic name; hydroxypropylmethylcellulose), and the mixture was stirred for achieving dispersion. Furthermore, methylene chloride (50 ml) was added to dissolve TC-5R completely, and after that, the solvent was evaporated.

The residue was dried overnight in vacuo at room temperature, and then milled and sieved (20 mesh) to give a solid dispersion composition.

EXAMPLE 2

A solid dispersion composition was produced from exifone (10 g) and TC-5R (2 g) according to a similar manner to that of Example 1.

EXAMPLE 3

A solid dispersion composition was produced from exifone (10 g) and TC-5R (10 g) according to a similar manner to that of Example 1.

EXAMPLE 4

A solid dispersion composition was produced from exifone (10 g) and TC-5R (30 g) according to a similar manner to that of Example 1.

EXAMPLE 5

A solid dispersion composition was produced from exifone (10 g) and TC-5R (50 g) according to a similar manner to that of Example 1.

EXAMPLE 6

Exifone (10 g) was dissolved in ethanol (150 ml), then TC-5R (5 g) was added to and dispersed in this solution, and methylene chloride (50 ml) was added for complete dissolution of TC-5R. To the solution obtained was added and therein dispersed Explotab (2.5 g) (trademark; product of Kimura Sangyo; generic name: carboxymethylstarch sodium). The solvent was evaporated, and the residue was dried overnight in vacuo at room temperature, then milled and sieved (20 mesh) to give a solid dispersion composition. [II] Process to mix the substances

EXAMPLE 7

Exifone (10 g) was placed, together with TC-5R (5 g) and Explotab (2.5 g), in a polyethylene bag, and the contents were mixed by shaking it well to give a mixed powder comprising TC-5R-treated exifone.

EXAMPLE 8

Exifone (10 g) and TC-5R (5 g) were placed in a polyethylene bag, and the contents were mixed by shaking it well, then the mixture was milled in a coffee mill for 5 minutes. Explotab (2.5 g) was added to the milled mixture, and the whole was placed in a polyethylene bag and mixed by shaking it well to give a mixed powder comprising TC-5R-treated exifone.

EXAMPLE 9

After exifone (10 g) and TC-5R (0.5 g) were mixed together in a beaker, the resulting mixture was then kneaded with a 20% aqueous ethanol solution (4 ml) and granulated. After dried in vacuo, the granules were milled in a mortar to an appropriate size and filled into No. 0 capsules to give a capsulated composition.

The formulation per one capsule was as follows:

| | |
|---|---|
| Exifone | 200 mg |
| TC-5R | 10 mg |
| | 210 mg |

EXAMPLE 10

A capsulated composition having the following formulation was produced from exifone (10 g) and HPC-L (0.5 g) (trademark; product of Nippon Soda; generic name: hydroxypropylcellulose) according to a similar manner to that of Example 9:

| | |
|---|---|
| Exifone | 200 mg |
| HPC-L | 10 mg |
| | 210 mg |

EXAMPLE 11

Exifone (10 g) was mixed with TC-5R (1.5 g) in a beaker, and then the mixture was kneaded with a 20% aqueous ethanol solution (5 ml) and granulated. After dried in vacuo, the granules were milled in a mortar and then placed with Explotab (0.35 g) in a polyethylene bag and the mixture was mixed by shaking the bag well to give a TC-5R-treated powder. This mixed powder was filled into No. 0 capsules to give a capsulated composition, each capsule having the following formulation:

| | |
|---|---|
| Exifone | 200 mg |
| TC-5R | 30 mg |
| Explotab | 7 mg |
| | 237 mg |

EXAMPLE 12

To the mixed powder comprising TC-5R-treated exifone as obtained according to a similar manner to that of Example 11 was added magnesium stearate (0.15 g) and tabletted by a single punch tabletting machine to give tablets, each having the following formulation:

| | |
|---|---|
| Exifone | 200 mg |
| TC-5R | 30 mg |
| Explotab | 7 mg |
| Magnesium stearate | 3 mg |
| | 240 mg |

EXAMPLE 13

A capsulated composition was produced from exifone (10 g) and TC-5R (2.5 g) according to a similar manner to that of Example 9, each capsule having the following formulation:

| | |
|---|---|
| Exifone | 200 mg |
| TC-5R | 50 mg |
| | 250 mg |

EXAMPLE 14

A capsulated composition was produced from exifone (10 g), TC-5R (2.5 g) and Explotab (2.5 g) according to a similar manner to that of Example 11, each capsule having the following formulation:

| | |
|---|---|
| Exifone | 200 mg |
| TC-5R | 50 mg |
| Explotab | 50 mg |
| | 300 mg |

EXAMPLE 15

A capsulated composition was produced from exifone (10 g), TC-5R (5 g) and Explotab (2.5 g) according to a similar manner to that of Example 11, each capsule having the following formulation:

| | |
|---|---|
| Exifone | 200 mg |
| TC-5R | 100 mg |
| Explotab | 50 mg |
| | 350 mg |

EXAMPLE 16

A capsulated composition was produced from exifone (10 g), TC-5R (10 g) and Explotab (5 g) according to a similar manner to that of Example 11, each capsule having the following formulation:

| | |
|---|---|
| Exifone | 100 mg |
| TC-5R | 100 mg |
| Explotab | 50 mg |
| | 250 mg |

EXAMPLE 17

A capsulated composition was produced from exifone (10 g), TC-5R (30 g) and Explotab (20 g) according to a similar manner to that of Example 11, each capsule having the following formulation:

| | |
|---|---|
| Exifone | 50 mg |
| TC-5R | 150 mg |
| Explotab | 100 mg |
| | 300 mg |

EXAMPLE 18

A capsulated composition was produced from exifone (10 g), TC-5R (50 g) and Explotab (20 g) according to a similar manner to that of Example 11, each capsule having the following formulation:

| | |
|---|---|
| Exifone | 50 mg |
| TC-5R | 250 mg |
| Explotab | 100 mg |
| | 400 mg |

EXAMPLE 19

Exifone (200 g) and TC-5R (100 g) were mixed with each other by shaking well in a polyethylene bag, the mixture was then kneaded with a 20% aqueous ethanol solution (80 ml) as a kneading solvent and granulated using a Planetary mixer for kneading. The granules obtained were dried at 40° C. in vacuo and then milled using Tornado type mill (20 mesh). The powder obtained was mixed with Explotab (27 g) in a polyethylene bag, and the resulting mixture was filled into No. 0 capsules to give a capsulated composition, each having the following formulation:

| | |
|---|---|
| Exifone | 200 mg |
| TC-5R | 100 mg |
| Explotab | 27 mg |
| | 327 mg |

EXAMPLE 20

(1) To the TC-5R-treated powder (before filling into capsules) obtained in Example 19 was added Explotab, Avicel (trademark; product of Asahi Chemical Industry; generic name: microcrystallinecellulose) and magnesium stearate, and then the mixture was tableted in the conventional manner to give tablets each having the following formulation:

| Exifone | 200 mg |
|---|---|
| TC-5R | 100 mg |
| Explotab | 37 mg |
| Avicel | 20 mg |
| Magnesium stearate | 3 mg |
| | 360 mg |

(2) The above tablets were film-coated by a conventional method to give film-coated tablets. The formulation of film coat layer per tablet was as follows:

| TC-5R | 5.4 mg |
|---|---|
| Polyethylene glycol 6000 | 0.8 mg |
| Titanium oxide | 1.7 mg |
| Yellow iron sesquioxide | 0.1 mg |
| | 8.0 mg |

EXAMPLE 21

Exifone (750 g), TC-5R (375 g), Explotab (101.25 g), lactose (678.75 g) and avicel (678.75 g) were mixed, granulated with an aqueous solution of citric acid (18.75 g), dried and sieved in a conventional method to give granules (2540 g). The granules obtained were mixed with magnesium stearate (33.08 g) and then tabletted in a conventional manner. The tablets thus obtained were film-coated in a conventional method to give film-coated tablets, each having the following formulation:

| Core Tablet | |
|---|---|
| Exifone | 40 mg |
| TC-5R | 20 mg |
| Explotab | 5.4 mg |
| citric acid | 1 mg |
| lactose | 35.6 mg |
| Avicel | 36.2 mg |
| magnesium stearate | 1.8 mg |
| | 140 mg |

| Film Coat Layer | |
|---|---|
| TC-5R | 3.8 mg |
| Polyethylene glycol 6000 | 0.5 mg |
| titanium oxide | 0.56 mg |
| yellow ferric oxide | 0.14 mg |
| carnauba wax | trace |
| | 5 mg |

In the pharmaceutical composition of the present invention the solubility of exifone was markedly improved as compared with the exifone bulk substance and, when orally administered, a sufficient bioavailability can be obtained.

In the following, for demonstrating the above fact, we set forth the dissolution test results and absorption test results (in dogs) obtained with several representative pharmaceutical compositions produced in accordance with the present invention.

Dissolution test 1

[I] Compositions tested

| Composition A | The solid dispersion composition obtained in Example 1 (exifone: TC-5R = 1:0.5) |
|---|---|
| Composition B | The solid dispersion composition obtained in Example 4 (exifone: TC-5R = 1:3) |
| Control composition | Exifone bulk substance (200 mg) filled in a No. 0 capsule |

[II] Test method

The dissolution percent was determined with passage of the time by the dissolution test method (2nd method) prescribed in the 11th edition of The Pharmacopoeia of Japan. The test conditions were as follows:

| Dissolution tester | Toyama Sangyo model |
|---|---|
| Sample quantity | 200 mg as exifone |
| Test Solution and its quantity | 1st fluid (pH 1.2), 900 ml |
| Paddle speed | 100 rpm |
| Measurement | uv wavelength 385 nm |

[III] Test results

The dissolution percent obtained at each measurement time was as follows:

| | Time (minutes) | |
|---|---|---|
| Test composition | 30 | 60 |
| Composition A | 77.0 | 89.0 |
| Composition B | 33.0 | 48.0 |
| Control composition | 11.4 | 12.4 |

The above test results clearly shows that in the pharmaceutical composition of the present invention produced by the process to convert the substances to a solid dispersion composition their dissolution patterns were markedly improved as compared with the exifone bulk substance. The drawback of exifone, its sparing solubility, has thus been markedly improved.

Dissolution test 2

[I] Composition tested

| Composition C | The mixed powder comprising TC-5R-treated exifone obtained in Example 7 (exifone: TC-5R = 1:0.5) |
|---|---|
| Composition D | The capsule containing a mixed powder comprising TC-5R-treated exifone obtained in Example 9 (exifone: TC-5R = 1:0.05) |
| Composition E | The capsule containing a mixed powder comprising HPC-L-treated exifone obtained in Example 10 (exifone: HPC-L = 1:0.05) |
| Composition F | The tablet comprising a mixed powder comprising TC-5R-treated exifone obtained in Example 12 (exifone: TC-5R = 1:0.15) |
| Composition G | The capsule containing a mixed powder comprising TC-5R-treated exifone obtained in Example 13 (exifone: TC-5R = 1:0.25) |
| Composition H | The capsule containing a mixed powder comprising TC-5R-treated exifone obtained in Example 15 (exifone: TC-5R = 1:0.5) |
| Control composition | The same control composition as used in Dissolution test 1. |

[II] Test method

The same method as used in Dissolution test 1 was used.

[III] Test results

The dissolution percent obtained at each measurement time was as follows:

| Test composition | Time (minutes) | |
|---|---|---|
| | 30 | 60 |
| Composition C | 52.1 | 68.1 |
| Composition D | 78.4 | 83.1 |
| Composition E | 68.3 | 71.7 |
| Composition F | 85.8 | 88.6 |
| Composition G | 80.2 | 93.8 |
| Composition H | 81.6 | 84.9 |
| Control composition | 11.4 | 12.4 |

The above test results show that in the pharmaceutical compositions of the present invention as produced by the process to mix the substances, whether in the form of mere mixtures or in any of the various dosage forms derived therefrom and in any of the varied mixing ratios, their dissolution patterns were markedly improved as compared with the exifone bulk substance and that, therefore, the drawback of exifone, its sparing solubility, has been markedly improved.

Since it has been so far believed that mere mixing of a sparingly soluble medicinal substance with a water-soluble polymer can hardly be expected to result in an improved solubility, the finding that mere mixing may produce a marked improvement as in the pharmaceutical composition of the present invention may be said to be a quite unexpected one.

Dissolution test 3

[I] Compositions tested

| | |
|---|---|
| Composition I | The solid dispersion composition obtained in Example 6 filled in No. 0 capsules in an amount of 200 mg as exifone per capsule (exifone: TC-5R = 1:0.5) |
| Composition J | The capsule containing a mixed powder comprising TC-5R-treated exifone obtained in Example 19 (exifone: TC-5R = 1:0.5) |
| Composition K | The film-coated tablet comprising a mixed powder comprision TC-5R-treated exifone obtained in Example 21 (exifone: TC-5R = 1:0.5) |
| Control composition | The same control composition as used in Dissolution test 1. |

[II] Test method

The same method as used in Dissolution test 1 was used.

[III] Test results

The dissolution percent obtained at each measurement time was as follows:

| Test composition | Time (minutes) | | | | |
|---|---|---|---|---|---|
| | 5 | 15 | 30 | 60 | 120 |
| Composition I | 22.9 | 64.0 | 77.5 | 83.5 | 87.5 |
| Composition J | 33.1 | 60.5 | 70.8 | 72.9 | 81.7 |
| Composition K | 13.4 | 61.8 | 74.5 | 79.1 | 79.1 |
| Control composition | 10.4 | 10.5 | 11.4 | 12.4 | 16.0 |

For demonstrating that an improvement in dissolution behavior can lead to an improvement in absorption upon oral administration, an absorption tests were performed in dogs using the representative pharmaceutical compositions of the present invention. The results are shown below.

Absorption test 1

[I] Compositions tested

Composition I, Composition J and Control composition, as used in Dissolution test 3 were used.

[II] Test method

The absorption test was performed in six male beagle dogs (weighing 9.0–11.5 kg; fasted from the previous day) by the three-way cross-over method.

The dose was 200 mg as exifone per dog (1 capsule of each test composition) and the test compositions were administered orally. After administration, blood samples were taken from the antebrachial vein with passage of the time and immediately assayed for exifone by the HPLC method.

[III] Test results

Plasma concentrations at each measurement time after oral administration, maximum plasma concentrations ($C_{max}$), times required for the plasma concentration to reach a maximum ($T_{max}$), and areas under the plasma concentration-time curve ($AUC_{0-6}$) are shown in the following table. Each data is given in terms of "mean±standard error".

| Test composition | Plasma concentration (μg/ml) Time | | | | | | |
|---|---|---|---|---|---|---|---|
| | 15 min | 30 min | 60 min | 120 min | 180 min | 240 min | 360 min |
| Composition I | 1.12 ±0.56 | 2.12 ±0.55 | 1.08 ±0.18 | 0.39 ±0.04 | 0.22 ±0.07 | 0.15 ±0.07 | 0.13 ±0.06 |
| Composition J | 0.99 ±0.45 | 1.28 ±0.22 | 0.96 ±0.13 | 0.54 ±0.12 | 0.19 ±0.06 | 0.18 ±0.06 | 0.15 ±0.07 |
| Control composition | 0.07 ±0.05 | 0.15 ±0.07 | 0.14 ±0.06 | 0.20 ±0.07 | 0.11 ±0.07 | 0.07 ±0.07 | 0.10 ±0.10 |

| Test compound | $C_{max}$ (μg/ml) | $T_{max}$ (hr) | $AUC_{0-6}$ (μg·hr/ml) |
|---|---|---|---|
| Composition I | 2.18 ±0.55 | 0.60 ±0.10 | 2.86 ±0.20 |
| Composition J | 1.50 ±0.36 | 0.50 ±0.11 | 2.59 ±0.41 |

| | | | |
|---|---|---|---|
| -continued | | | |
| Control composition | 0.30 ±0.06 | 1.58 ±0.58 | 0.69 ±0.17 |

Absorption test 2

[I] Compositions tested

Composition J and Composition K as used in Dissolution test 3 were used.

[II] Test method

The absorption test was performed in six male beagle dogs (weighing 9.0–11.5 kg; fasted from the previous day) by the two-way cross-over method.

The dose was 200 mg as exifone per dog (1 capsule of Composition J and 5 tablets of Composition K) and the test composition were administered orally. After administration, blood samples were taken from the antebrachial vein with passage of the time and immediately assayed for exifone by the HPLC method.

[III] Test results

Plasma concentrations at each measurement time after oral administration, maximum plasma concentrations ($C_{max}$), times required for the plasma concentration to reach a maximum ($T_{max}$), and areas under the plasma concentration-time curve ($AUC_{0-8}$) are shown in the following table. Each data is given in terms of "mean±standard error".

| Test compo- sition | Plasma concentration (μg/ml) Time | | | | | | | |
|---|---|---|---|---|---|---|---|---|
| | 15 min | 30 min | 60 min | 120 min | 180 min | 240 min | 360 min | 480 min |
| Compo- sition J | 0.50 ±0.75 | 1.20 ±0.70 | 1.01 ±0.36 | 0.56 ±0.34 | 0.42 ±0.43 | 0.38 ±0.46 | 0.15 ±0.07 | 0.13 ±0.08 |
| Compo- sition K | 0.74 ±0.84 | 1.47 ±0.37 | 0.96 ±0.06 | 0.47 ±0.28 | 0.20 ±0.05 | 0.16 ±0.07 | 0.14 ±0.04 | 0.13 ±0.05 |

| Test compound | $C_{max}$ (μg/ml) | $T_{max}$ (hr) | $AUC_{0-8}$ (μg · hr/ml) |
|---|---|---|---|
| Composition J | 1.52 ±0.39 | 1.33 ±1.35 | 3.34 ±0.88 |
| Composition K | 1.66 ±0.34 | 0.50 ±0.15 | 2.78 ±0.42 |

The above test results clearly show that, as expected on the basis of the results of Dissolution test 3, in the pharmaceutical compositions of the present invention, whether obtained by the process to convert the substances to a solid dispersion composition or by the process to mix the substances, the absorbability into the blood circulation were markedly increased as compared with the exifone bulk substance.

In view of the results of the various tests mentioned above, it is apparent that, in the pharmaceutical composition of the present invention which comprises exifone and a water-soluble polymer, both the drawback of exifone, namely, its being sparingly soluble in water, and the low absorbability into blood circulation upon oral administration, which is due to the sparing solubility of exifone, have been improved to a remarkable extend, and so the pharmaceutical composition of the present invention which comprises exifone and a water-soluble polymer is very useful.

What we claim is:

1. A pharmaceutical composition comprising a physical mixture of exifone and a water solubilizing effective amount of at least one water soluble derivative selected from the group consisting of hydroxypropylmethylcellulose, hydroxypropylcellulose and methylcellulose.

2. The composition of claim 1 wherein said exifone and said derivative are present in a ratio of about 1:0.01 to about 1:7 by weight.

* * * * *